US 8,591,955 B2
Nov. 26, 2013

(12) United States Patent
Fujiwara

(10) Patent No.: US 8,591,955 B2
(45) Date of Patent: *Nov. 26, 2013

(54) ORALLY RAPIDLY DISINTEGRATING TABLET THAT CONTAINS TWO OR MORE TYPES OF PARTICLES

(75) Inventor: Keiichi Fujiwara, Ibaraki (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/389,280

(22) PCT Filed: Aug. 11, 2010

(86) PCT No.: PCT/JP2010/063599
§ 371 (c)(1),
(2), (4) Date: Feb. 7, 2012

(87) PCT Pub. No.: WO2011/019043
PCT Pub. Date: Feb. 17, 2011

(65) Prior Publication Data
US 2012/0135991 A1 May 31, 2012

(30) Foreign Application Priority Data

Aug. 11, 2009 (JP) ................ 2009-186643

(51) Int. Cl.
*A61K 9/50* (2006.01)
(52) U.S. Cl.
USPC ........................................................ 424/499
(58) Field of Classification Search
None
See application file for complete search history.

(56) References Cited

U.S. PATENT DOCUMENTS

| 7,465,864 B2 | 12/2008 | Heintz |
| 2006/0204572 A1* | 9/2006 | Higuchi et al. ............... 424/464 |
| 2007/0148230 A1 | 6/2007 | Fujiwara et al. |
| 2007/0275058 A1 | 11/2007 | Tanaka et al. |

FOREIGN PATENT DOCUMENTS

| CN | 1856298 | 11/2006 |
| CN | 1913876 | 2/2007 |
| EP | 1 329 217 | 7/2003 |
| JP | 2000-086537 | 3/2000 |
| JP | 2005-139168 | 6/2005 |
| WO | 2005/037254 | 4/2005 |
| WO | 2005/055989 | 6/2005 |
| WO | 2007/029376 | 3/2007 |
| WO | 2009/066773 | 5/2009 |
| WO | 2009/102038 | 8/2009 |

OTHER PUBLICATIONS

International Preliminary Report on Patentability and Written Opinion issued Mar. 13, 2012 in International Application No. PCT/JP2010/063599, of which the present application is the national stage.

International Search Report issued Oct. 26, 2010 in International (PCT) Application No. PCT/JP2010/063599, of which the present application is the national stage.

Supplementary European Search Report issued Jan. 4, 2013 in corresponding European Application No. 10808226.4.

\* cited by examiner

*Primary Examiner* — Carlos Azpuru

(74) *Attorney, Agent, or Firm* — Wenderoth, Lind & Ponack, L.L.P.

(57) ABSTRACT

The present invention provides an orally rapidly-disintegrating tablet comprising at least two particles. Regarding medicaments with unpleasant taste, the present invention provides a tablet comprising such medicament having a suitable hardness so that the tablet can be handled without any difficulty in the period from the formulation of the tablet to the administration thereof (in particular, a tablet which can maintain the hardness thereof when it is stored under a humidified condition); a small size; no unpleasant taste; a pleasant feeling in a mouth after administration; and an excellent disintegration character in the oral cavity and an excellent dissolution character in the gastrointestinal tract.

14 Claims, No Drawings

ORALLY RAPIDLY DISINTEGRATING TABLET THAT CONTAINS TWO OR MORE TYPES OF PARTICLES

TECHNICAL FIELD

The present invention relates to an orally rapidly-disintegrating tablet comprising at least two particles. In detail, the present invention relates to a formulation which can maintain the same hardness as general tablets and also maintain a suitable hardness to be handled after taken out from the package, and can rapidly disintegrate in the oral cavity without water.

BACKGROUND ART

Due to an aging society, it has been desired to develop an orally rapidly-disintegrating tablet which can be easily taken by patients having difficulty in swallowing tablets such as elderly people and also children. Furthermore, it is useful to develop an orally rapidly-disintegrating tablet not only for elderly people or children but also for other patients because of the convenience of an orally rapidly-disintegrating tablet (i.e. an orally rapidly-disintegrating tablet can be taken without water).

However, there is a problem in using an orally rapidly-disintegrating tablet in the same manner as ordinary tablets because it is difficult to maintain the hardness of an orally rapidly-disintegrating tablet after taken out from the package. In the conventional art, there seems to be no disclosures about the hardness, or even if there are, such disclosures merely describe how hard an initial hardness of a tablet needs to be in case that the tablet is taken out from the package. There seems to be no disclosure teaching that the hardness of the tablet would decrease after taken out from the package. An orally rapidly-disintegrating tablet is required to have a short disintegration time in the oral cavity, and a suitable hardness to prevent the tablet from being chipped or powdered in manufacturing or transporting the tablet. However, hardness and disintegration time are conflicting factors, and in general, when disintegration time is shortened, hardness will be decreased, and when hardness is increased, disintegration time will be expanded. In order to solve the problem of the two conflicting factors (i.e. disintegration time and hardness), it is known to use processes such as wet compression methods and heat compression methods. However, the problem is that the said methods cannot be carried out with typical equipments for compressing/shaping formulations, and the said methods require special equipments such as warming devices, humidification devices, and drying devices.

Furthermore, it is known to add an additive agent to the orally rapidly-disintegrating tablet as a different means in order to solve the above-mentioned problem. As an example of such additive agent, Patent Reference 1 discloses a composition for pharmaceuticals which can be obtained by homogeneously dispersing an inorganic compound and a saccharide to give a suspension, and then spray-drying the suspension. Patent Reference 2 discloses a composition which can be obtained by spray-drying a suspension of a saccharide (i.e. a combination of mannitol and xylitol), an inorganic excipient and a disintegrant; and also discloses an orally rapidly-disintegrating tablet comprising the composition. Patent Reference 3 discloses an orally rapidly-disintegrating tablet which comprises a step of using a disintegrating agent at the final stage of the formulation process.

Meanwhile, not a few medicaments have "unpleasant taste" which have, for example, a bitter taste, an astringent taste, and a pungent taste. When such medicament is contained in the orally rapidly-disintegrating tablet and dissolved in the oral cavity, it is often difficult to take the tablet. In particular, Patent Reference 4 describes a technique to formulate an orally rapidly-disintegrating tablet with such "medicament with unpleasant taste", which improves the unpleasant taste of the medicament by mixing a medicament with unpleasant taste, methylcellulose and mannitol, and then particulating the mixture.

[Patent Reference 1] JP 2000-086537 A
[Patent Reference 2] JP 2005-139168 A
[Patent Reference 3] WO 2007/029376
[Patent Reference 4] WO 2005/055989

SUMMARY OF INVENTION

Technical Problem

In general, an orally rapidly-disintegrating tablet is disintegrated with a small amount of saliva. Thus, the hardness of the tablet is easily decreased with humidity, and it is perceived to be difficult to develop an orally rapidly-disintegrating tablet which stably maintains its hardness. It has been therefore desired in clinical practice to provide an orally rapidly-disintegrating tablet which can sufficiently shorten the disintegration time in the oral cavity, and can maintain the initial hardness and also the hardness after taken out from the package.

Solution to Problem

In such a situation, the present inventors managed to prepare a formulation which has an excellent disintegration property in the oral cavity and a suitable initial-hardness by mixing (1) a medicament-containing particle prepared by particulating a mixture of a medicament, a water-soluble polymer and a sugar or sugar alcohol and (2) a spray-dried particle which is separately prepared by spray-drying specific ingredients, and then compressing the mixture. The present inventors have extensively studied various conditions to succeed in preventing the hardness of the tablet from decreasing after taken out from the package. Thus, the present invention has been completed.

The present invention provides various embodiments as follows.

Term 1

An orally rapidly-disintegrating tablet comprising the following particles (1) and (2):

(1) a medicament-containing particle comprising the following ingredients (a) to (c):
  (a) a medicament
  (b) a water-soluble polymer, and
  (c) a sugar or sugar alcohol
wherein all of the ingredients are granulated and then particulated, and (2) a spray-dried particle comprising the following ingredients (d) to (f):
  (d) mannitol, or mannitol and xylitol
  (e) carboxymethylcellulose, and
  (f) a disintegrant
wherein all of the ingredients are dispersed in a solvent for dispersion and then spray-dried.

Term 2

The orally rapidly-disintegrating tablet of Term 1 wherein the water-soluble polymer (b) is at least one compound selected from the group consisting of polyvinylpyrrolidone, methylcellulose, pullulan, polyvinyl alcohol, hydroxypropyl methylcellulose, and hydroxypropyl cellulose.

Term 3
The orally rapidly-disintegrating tablet of Term 2 wherein the water-soluble polymer (b) is at least one compound selected from the group consisting of methylcellulose, pullulan, polyvinyl alcohol, and hydroxypropyl cellulose.

Term 4
The orally rapidly-disintegrating tablet of any one of Terms 1 to 3 wherein the sugar or sugar alcohol (c) is at least one compound selected from the group consisting of mannitol, xylitol, lactose, erythritol, trehalose, sucrose, maltitol, and lactitol.

Term 5
The orally rapidly-disintegrating tablet of Term 4 wherein the sugar or sugar alcohol (c) is at least one compound selected from the group consisting of mannitol, xylitol, lactose, erythritol, and lactitol.

Term 6
The orally rapidly-disintegrating tablet of any one of Terms 1 to 5 wherein the disintegrant (f) is at least one compound selected from the group consisting of a low-substituted hydroxypropyl cellulose, croscarmellose sodium, microcrystalline cellulose, carmellose calcium, hydroxy-propyl starch, and rice starch.

Term 7
The orally rapidly-disintegrating tablet of Term 6 wherein the disintegrant (f) comprises a low-substituted hydroxypropyl cellulose.

Term 8
The orally rapidly-disintegrating tablet of any one of Terms 1 to 7 wherein the spray-dried particle (2) further comprises ingredient (g):
(g) an inorganic compound
and all of the ingredients (d) to (g) are dispersed in a solvent for dispersion and then spray-dried.

Term 9
The orally rapidly-disintegrating tablet of Term 8 wherein the inorganic compound (g) is at least one compound selected from the group consisting of magnesium aluminometasilicate, magnesium aluminosilicate, anhydrous silicic acid, light anhydrous silicic acid, calcium silicate, and dibasic calcium phosphate.

Term 10
The orally rapidly-disintegrating tablet of Term 1 wherein each content of:
(a) the medicament is 1 wt % to 30 wt %,
(b) the water-soluble polymer is 3 wt % to 45 wt %, and
(c) the sugar or sugar alcohol is 40 wt % to 90 wt %
per 100 wt % of the whole weight of the medicament-containing particle (1).

Term 11
The orally rapidly-disintegrating tablet of Term 1 wherein each content of:
(d) the mannitol, or mannitol and xylitol is 65 wt % to 95 wt %,
(e) the carboxymethylcellulose is 1 wt % to 20 wt %, and
(f) the disintegrant is 1 wt % to 20 wt %
per 100 wt % of the whole weight of the spray-dried particle (2).

Term 12
The orally rapidly-disintegrating tablet of Term 11 wherein the spray-dried particle (2) further comprises:
(g) an inorganic compound in an amount of 0.01 wt % to 15 wt %
per 100 wt % of the whole weight of the spray-dried particle (2).

Term 13
The orally rapidly-disintegrating tablet of any one of Terms 1 to 12 wherein the medicament (a) is 4-amino-5-chloro-2-ethoxy-N-[[4-(4-fluorobenzyl)-2-morpholinyl]-methyl]benzamide.

Term 14
The orally rapidly-disintegrating tablet of any one of Terms 1 to 13 wherein each content of:
the medicament-containing particle (1) is 5 wt % to 37 wt %, and
the spray-dried particle (2) is 15 wt % to 90 wt %
per 100 wt % of the whole weight of the orally rapidly-disintegrating tablet.

Term 15
The orally rapidly-disintegrating tablet of any one of Terms 1 to 14 wherein the medicament-containing particle (1) further comprises:
(3) Other Formulation Additives
and all of the ingredients in (1) are granulated and then particulated.

Term 16
The orally rapidly-disintegrating tablet of any one of Terms 1 to 15 wherein the spray-dried particle (2) further comprises:
(3) Other Formulation Additives
and all of the ingredients in (2) are dispersed in a solvent for dispersion and then spray-dried.

Effects of Invention

Regarding medicaments with unpleasant taste, the present invention can provide a tablet comprising such medicament which has the following properties:
a suitable hardness so that the tablet can be handled without any difficulty in the period from the formulation of the tablet to the administration thereof (in particular, a tablet which can maintain the hardness thereof when it is stored under a humidified condition),
a small size,
without any unpleasant taste,
a pleasant feeling in a mouth after administration, and
an excellent disintegration character in the oral cavity and an excellent dissolution character in the gastrointestinal tract; and
a bulk-production process thereof.

BEST MODE FOR CARRYING OUT INVENTION

The "orally rapidly-disintegrating tablet" used herein means a formulation (e.g. tablets) which does not require water when administration, and disintegrates within about 60 seconds (preferably within 40 seconds) in a test measured with mainly saliva in the oral cavity or an apparatus. The tablet used herein may be tested with an orally disintegrating tablet tester (manufactured by Toyama Sangyo, ODT-101).

The values of the "mean particle size" shown in the claims and the description are measured on, for example, a laser diffraction sensor (manufactured by Sympatec, HELOS & RODOS).

Throughout the claims and the description, when just "wt %" is used, it means a wt % per 100 wt % of the whole weight of the final formulation (per a tablet). On the other hand, when "wt %" for each ingredient is used per 100 wt % of the whole weight of the medicament-containing particle or the spray-dried particle, it means each content ratio that each ingredient is added when the particle is formulated.

The orally rapidly-disintegrating tablet of the present invention is an orally rapidly-disintegrating tablet comprising the following particles (1) and (2):

(1) a medicament-containing particle comprising the following ingredients (a) to (c):
(a) a medicament
(b) a water-soluble polymer, and
(c) a sugar or sugar alcohol
wherein all of the ingredients are granulated and then particulated, and (2) a spray-dried particle comprising the following ingredients (d) to (f):
(d) mannitol, or mannitol and xylitol
(e) carboxymethylcellulose, and
(f) a disintegrant
wherein all of the ingredients are dispersed in a solvent for dispersion, and then spray-dried. Hereinafter, each of the particles and the ingredients are explained.

(1) Medicament-Containing Particle (a) Medicament

An active ingredient used for the medicament herein should not be limited to a particular active ingredient, as long as it can be used for treating or preventing diseases as an active pharmaceutical ingredient and it can be taken by oral administration. The active ingredient includes, for example, analeptics, antipyretic analgesics, antipsychotic drugs, hypnotics, antispastic drugs, central nervous system agents, brain metabolic stimulants, cerebral circulation improvers, antiepileptic drugs, sympathomimetic drugs, stomachics and digestives, anti-ulcerogenic drugs, gastrointestinal motility improvers, antacids, cough medicines, antimotility agents, antiemetic drugs, respiratory stimulants, bronchodilators, antiallergic drugs, cardiac stimulants, antiarrhythmic agents, diuretic drugs, vasoconstrictors, coronary vasodilators, vasodilators, peripheral vasodilators, hypolipidemic agents, cholagogues, chemotherapeutic agents, agents for treating diabetic complication, osteoporosis drugs, antirheumatic drugs, skeletal muscle relaxants, antipodagrics, anticoagulant agents, and antineoplastic drugs. The active ingredient used herein may be in a salt or free form as long as it is pharmaceutically acceptable. Furthermore, the active ingredient used herein may be in the form of a solvate (e.g. alcoholate) or a hydrate. The above-mentioned active ingredients may be used alone or in a combination with two or more. In addition, the medicament used as a material may be masked beforehand to reduce the unpleasant taste (e.g. bitter taste) thereof.

In particular, the medicament used herein may be 4-amino-5-chloro-2-ethoxy-N-[[4-(4-fluorobenzyl)-2-morpholinyl]methyl]benzamide or a pharmaceutically acceptable salt thereof. The compound (or an acid addition salt or a hydrate thereof) is a selective serotonin 4 receptor agonist and exhibits an excellent gastrokinetic-effect. The compound is disclosed in U.S. Pat. No. 4,870,074 A. Patent Reference 4 discloses a particle obtained by combining the above-mentioned compound with mannitol and methylcellulose, but wherein neither working examples using a spraying-dried particle nor effects thereof are disclosed. The 4-amino-5-chloro-2-ethoxy-N-[[4-(4-fluorobenzyl)-2-morpholinyl]methyl]benzamide used herein may be in the form of a racemic mixture or an optically active substance comprising either of the racemic compound, but the racemic mixture is preferable. In addition, the compound may be in a free form or in a pharmaceutically acceptable salt form. A preferred salt is an acid addition salt. The organic acid addition salt used herein includes, for example, formate, acetate, lactate, adipate, citrate, tartrate, fumarate, methanesulfonate and maleate, but it should not be limited thereto. The inorganic acid addition salt used herein includes, for example, hydrochloride, sulfate, nitrate and phosphate, but it should not be limited thereto. Among the above-mentioned salts, citrate is especially preferable. In addition, the compound or a pharmaceutically acceptable salt thereof may be in the form of a solvate, a hydrate or a non-hydrate. It is preferably a citric acid hydrate thereof, and in particular, citric acid dihydrate.

The medicament is contained typically in an amount of 1 wt % to 30 wt %, preferably 4 wt % to 25 wt %, more preferably 5 wt % to 20 wt %, and even more preferably 9 wt % to 20 wt % per 100 wt % of the whole weight of the medicament-containing particle. In the present invention, in order to easily prepare a particle by mixing several ingredients including the medicament and a solvent prior to the tableting step, it is recommendable to micronize the medicament into a mean particle size of 1 μm to 30 μm, preferably 1 μm to 15 μm, more preferably 1 μm to 10 μm, and even more preferably 5 μm to 10 μm. In addition, the "active ingredient content" used herein is generally an amount based on the form of a "pharmaceutically active ingredient" used as a medicament. That is, when the medicament is in the form of a salt, the amount of acid or base which forms the salt is also added to the "active ingredient content". However, when the medicament has, for example, crystal water, the amount of crystal water is not included in the "active ingredient content".

(b) Water-Soluble Polymer

The water-soluble polymer used herein is one compound or a mixture of at least two compounds selected from the group consisting of polyvinylpyrrolidone, methylcellulose, pullulan, polyvinyl alcohol, hydroxypropyl methylcellulose, and hydroxypropyl cellulose, but it should not be limited thereto. The water-soluble polymer is preferably methylcellulose, pullulan, polyvinyl alcohol and/or hydroxypropyl cellulose; and more preferably methylcellulose. When the viscosity of 2 wt % aqueous solution of the water-soluble polymer is measured at 0° C. according to Japanese Pharmacopoeia 14th edition, the viscosity is typically 1 mm$^2$/sec to 100 mm$^2$/sec, preferably 5 mm$^2$/sec to 60 mm$^2$/sec, more preferably 10 mm$^2$/sec to 40 mm$^2$/sec, and even more preferably 20 mm$^2$/sec to 30 mm$^2$/sec. The content of the water-soluble polymer is typically 3 wt % to 45 wt %, preferably 3 wt % to 40 wt %, more preferably 5 wt % to 30 wt %, and even more preferably 10 wt % to 30 wt % per 100 wt % of the whole weight of the medicament-containing particle.

(c) Sugar or Sugar Alcohol

The sugar or sugar alcohol used herein is one compound or a mixture of at least two compounds selected from the group consisting of, for example, mannitol, xylitol, lactose, erythritol, trehalose, sucrose, maltitol, and lactitol, but it should not be limited thereto. The sugar or sugar alcohol is preferably mannitol, xylitol, lactose, erythritol and/or lactitol; more preferably mannitol; and even more preferably D-mannitol. The sugar or sugar alcohol is used in a suitable amount so that the tablet can be rapidly dissolved, and it is typically 40 wt % to 90 wt %, preferably 60 wt % to 90 wt %, more preferably 60 wt % to 85 wt %, and even more preferably 60 wt % to 75 wt % per 100 wt % of the whole weight of the medicament-containing particle.

The medicament-containing particle comprises the above ingredients (a) to (c) wherein all of the ingredients are granulated and then particulated. Specifically, the above ingredients (a) to (c) are mixed, granulated, and then particulated. More specifically, for example, the above ingredients (a) to (c) are mixed, a solvent is added to the mixture, and the mixture is granulated to obtain a particle. The said methods include a procedure comprising mixing all of the ingredients, adding a solvent to the mixture, and then granulating the wet mixture; and a procedure comprising dissolving or suspending a part or all of the ingredients in a solvent, adding the solution or suspension to the mixture of the ingredients, and then granulating the resultant mixture. Moreover, the medicament-containing particle can be granulated by further adding the below-mentioned formulation additives (e.g. binder and corrigent) as long as the effect of the present invention is not decreased. The granulation method used herein is a common granulation method such as a mixing granulation method, an extrusion granulation method, a fluidized bed granulation method, and a dry granulation method. The solvent used herein may be any solvent as long as the solvent does not affect the property of the composition and is acceptable to use for pharmaceutical agents or foods from the viewpoint of stability and safety; and such solvent is includes one compound or a mixed solvent of at least two compounds selected from the group consisting of, for example, water, ethanol, and methanol, but it should not be limited thereto. Regarding the "medicament-containing particle" used herein, the medicament is not completely coated with the water-soluble polymer, and a part of the medicament may exist on the surface of the particle.

The medicament-containing particle is contained typically in an amount of 5 wt % to 37 wt %, preferably 10 wt % to 30 wt %, more preferably 10 wt % to 25 wt %, even more preferably 10 wt % to 20 wt %, and most preferably 10 wt % to 15 wt % per 100 wt % of the orally rapidly-disintegrating tablet. Furthermore, the mean particle size of the medicament-containing particle before formulating into a tablet is typically 500 μm or less, for example 50 μm to 500 μm, preferably 50 μm to 400 μm, more preferably 100 μm to 300 μm, even more preferably 100 μm to 200 μm, and most preferably 100 μm to 150 μm.

(2) Spray-Dried Particle (d) Mannitol, or Mannitol and Xylitol

The mannitol, or mannitol and xylitol is contained typically in an amount of 65 wt % to 95 wt % per 100 wt % of the whole weight of the spray-dried particle. The amount of mannitol alone or the total amount of mannitol and xylitol is preferably 70 wt % to 90 wt %, more preferably 70 wt % to 85 wt %, and even more preferably 75 wt % to 85 wt % per 100 wt % of the whole weight of the spray-dried particle. When xylitol is used in the spray-dried particle, the xylitol is contained typically at 0.01 wt % to 5 wt %, preferably 2 wt % to 5 wt %, more preferably 2 wt % to 4 wt %, and even more preferably 2 wt % to 3 wt % per 100 wt % of the whole weight of the spray-dried particle.

(e) Carboxymethylcellulose

The carboxymethylcellulose (optionally referred to as "carmellose" herein) used herein is contained typically in an amount of 1 wt % to 20 wt %, preferably 3 wt % to 15 wt %, more preferably 3 wt % to 12 wt %, even more preferably 5 wt % to 12 wt %, and most preferably 5 wt % to 10 wt %.

(f) Disintegrant

The disintegrant used herein is one compound or a mixture of at least two compounds selected from the group consisting of, for example; a low-substituted hydroxypropyl cellulose, croscarmellose sodium, microcrystalline cellulose, carmellose calcium, hydroxypropyl starch, rice starch and carmellose sodium, but it should not be limited thereto. The disintegrant is preferably a low-substituted hydroxypropyl cellulose, croscarmellose sodium, micro-crystalline cellulose, carmellose calcium, hydroxypropyl starch and/or rice starch; and most preferably a low-substituted hydroxypropyl cellulose. The low-substituted hydroxypropyl cellulose used herein means a hydroxypropyl cellulose in which hydroxypropyl group is contained in an amount of 5 wt % to 16 wt %.

The disintegrant is contained typically in an amount of 1 wt % to 20 wt %, preferably 3 wt % to 15 wt %, more preferably 3 wt % to 12 wt %, even more preferably 5 wt % to 12 wt %, and most preferably 5 wt % to 10 wt % per 100 wt % of the whole weight of the spray-dried particle.

(g) Inorganic Compound

The spray-dried particle of the present invention may further comprise an inorganic compound. The disintegration time can be further shortened by mixing an inorganic compound to the spray-dried particle. The inorganic compound used herein is one compound or a mixture of at least two compounds selected from the group consisting of, for example, magnesium aluminometasilicate, magnesium aluminosilicate, anhydrous silicic acid, light anhydrous silicic acid, calcium silicate, and dibasic calcium phosphate, but it should not be limited thereto. A preferred inorganic compound is magnesium alumino-metasilicate and/or calcium silicate. The inorganic compound is typically in an amount of 0.01 wt % to 15 wt %, preferably 3 wt % to 12 wt %, more preferably 3 wt % to 10 wt %, even more preferably 4 wt % to 8 wt %, and most preferably 4 wt % to 5 wt % per 100 wt % of the whole weight of the spray-dried particle.

The spray-dried particle comprises the above ingredients (d) to (f) and optionally comprises the above ingredient (g), wherein all of the ingredients are dispersed in a solvent for dispersion and then spray-dried. Specifically, the above ingredients (d) to (f) and the optional ingredient (g) are added at the same time or added separately to a solvent for dispersion, mixed and then spray-dried. The spray-dried particle can be prepared by, for example, dissolving or dispersing the ingredients in a solvent to obtain an aqueous solution or an aqueous dispersion, and then spray-drying the solution or dispersion.

The solvent for dispersion used herein may be any solvent as long as the solvent does not affect the property of the composition and is acceptable to use for pharmaceutical agents or foods from the viewpoint of stability and safety; and such solvent is one compound or a mixed solvent of at least two compounds selected from the group consisting of, for example, water, ethanol, and methanol, but it should not be limited thereto. The condition of spray-drying is not limited to a particular manner, but it is preferable to use a rotary atomizer or a nozzle atomizer in the spray-drying procedure. Regarding the spray-drying temperature, the inlet temperature is preferably about 120° C. to 220° C., and the outlet temperature is preferably about 80° C. to 130° C. The dispersion can be prepared by well-known methods (e.g. stirring in a typical manner, colloid mill, high-pressure homogenizer, and ultrasonication) or any other methods as long as the particle can be homogenously dispersed in the aqueous dispersion. The amount of the spray-dried particle contained in the dispersion is not limited to a particular amount as long as the dispersion has a suitable viscosity to be spray-dried, and the amount thereof is typically 5 wt % to 50 wt % and preferably 10 wt % to 45 wt %.

The spray-dried particle is contained typically in an amount of 15 wt % to 90 wt %, preferably 30 wt % to 85 wt %, more preferably 40 wt % to 85 wt %, even more preferably 40 wt % to 80 wt %, and most preferably 60 wt % to 80 wt % per 100 wt % of the orally rapidly-disintegrating tablet. When the content of the medicament-containing particle is high, the content of the spray-dried particle can be optionally reduced. The mean particle size of the spray-dried particle before formulating into a tablet is typically 400 μm or less, for example 1 μm to 400 μm, and preferably 5 μm to 300 μm.

(3) Other Formulation Additives

The particles of the above-mentioned (1) and (2) are the essential ingredients of the orally rapidly-disintegrating tablet of the present invention, but the tablet is generally formulated by adding other formulation additives thereto. The formulation additives may be optionally:

(a) added into the particles of (1) or (2);
(b) used as an additive out of the particles of (1) and (2); or
(c) added in manner of both (a) and (b).

The "other formulation additives" which may be used herein includes any additive(s), as long as there are no problems in the stability of the medicament or in the formulation when the additive(s) is mixed. The other formulation additive(s) is one compound or at least two compounds selected from the group consisting of, for example, a lubricant, a corrigent, a binder, an excipient, a stabilizing agent, a surfactant, a fluidizer, a colorant and a flavoring agent, but it should not be limited thereto. The "other formulation additives" is contained in an amount of 0.01 wt % to 25 wt %, preferably 0.1 wt % to 25 wt %, more preferably 0.1 wt % to 10 wt %, and even more preferably 0.1 wt % to 1 wt %.

Lubricant

The lubricant used herein may be mixed inside the tablet. The lubricant is one compound or at least two compounds selected from the group consisting of, for example, stearic acid, a metallic stearate, a sucrose fatty acid ester, talc, hardened oil and macrogol, but it should not be limited thereto. The metallic stearate includes, for example, magnesium stearate, calcium stearate and aluminum monostearate, but it should not be limited thereto. Among the above-mentioned lubricants, magnesium stearate is preferable. The mean particle size of the lubricant before formulated into a tablet is 0.5 μm to 50 μm, preferably 1 μm to 30 μm, and more preferably 1 μm to 10 μm. The stearic acid or metallic stearate in the formulation is contained in an amount of typically 0.01 wt % to 2.0 wt %, preferably 0.1 wt % to 1.0 wt %, more preferably 0.1 wt % to 0.8 wt %, and even more preferably 0.2 wt % to 0.5 wt %.

Corrigent

A corrigent may be mixed in the present invention. Specifically, the corrigent used herein includes, for example, neotame, thaumatin, aspartame, stevia, saccharin sodium and sodium glutamate, but it should not be limited thereto. The above-mentioned corrigent may be used alone, or two or more of them may be used in combination.

Binder

Specifically, the binder used herein includes, for example, Acacia, starch, hydroxypropyl cellulose, hydroxypropyl methylcellulose, polyvinyl alcohol, pullulan, gelatin, ethylcellulose, methylcellulose, carmellose sodium, dextrin and povidone, but it should not be limited thereto. The content of the binder is not limited to a particular amount, as long as the tablet maintains its hardness and is disintegrated in the oral cavity without any trouble.

Excipient

Specifically, the excipient used herein includes, for example, lactose, sucrose, mannitol, starch, micro-crystalline cellulose (e.g. Ceolus KG-802), erythritol, trehalose, anhydrous dibasic calcium phosphate and calcium sulfate, but it should not be limited thereto.

Stabilizing Agent

Specifically, the stabilizing agent used herein includes, for example, disodium edetate and tocopherol, but it should not be limited thereto.

Surfactant

Specifically, the surfactant used herein includes, for example, sodium lauryl sulfate, polysorbate and hardened oil, but it should not be limited thereto.

Fluidizer

Specifically, the fluidizer used herein includes, for example, light anhydrous silicic acid and magnesium aluminometasilicate, but it should not be limited thereto.

Colorant

Specifically, the colorant used herein includes, for example, edible dye, iron sesquioxide and carmine, but it should not be limited thereto.

Flavoring Agent

Specifically, the flavoring agent used herein includes, for example, various fruit flavors (e.g. strawberry flavor), yogurt, mint and menthol, but it should not be limited thereto.

Orally Rapidly-Disintegrating Tablet and Process Thereof

The orally rapidly-disintegrating tablet of the present invention can be prepared by a method conventionally used in the field of formulation. The present invention can be prepared by, for example, homogeneously mixing the medicament-containing particle, the spray-dried particle and the above-mentioned formulation additives, and then formulating the mixture by a well-known procedure. The mixture can be formulated into various solid formulations which are suitable for oral administration (e.g. tablets, granules, pills, powders, and fine grain agents). For example, a tablet may be obtained by compressing a mixture of the medicament-containing particle, the spray-dried particle, and the formulation additives on a typical tablet press machine or on a tablet press machine whose punch and die are coated with stearic acid or a metallic stearate.

The orally rapidly-disintegrating tablet obtained in the above-mentioned process is rapidly, disintegrated in the oral cavity and also shows a suitable hardness. The disintegration time of the orally rapidly-disintegrating tablet of the present invention is measured on the below-mentioned orally disintegrating tablet tester (manufactured by Toyama Sangyo Co., Ltd., ODT-101), and it is typically about 60 seconds or less, and preferably about 40 seconds or less. Furthermore, the hardness measured on the below-mentioned tablet hardness tester (manufactured by Toyama Sangyo Co., Ltd., TH-203MP) is typically 30 N to 70 N, and preferably 40 N to 60 N. After storing the tablet for one day at 25° C./75% RH, the hardness thereof is typically 30 N to 60 N, and preferably 35 N to 55 N, wherein the hardness was measured by a general method on a tablet hardness tester (manufactured by Toyama Sangyo Co., Ltd., TH-203MP).

EXAMPLE

Hereinafter, the present invention is illustrated in more detail but it should not be limited thereto.

The mosapride citrate dihydrate used herein is (±)-4-amino-5-chloro-2-ethoxy-N-[[4-(4-fluorobenzyl)-2-morpholinyl]methyl]benzamide citrate dihydrate, and is supplied by Dainippon Sumitomo Pharma Co., Ltd. (mean particle size: about 5 μm). The methylcellulose used herein is Metolose SM-25 supplied by Shin-Etsu Chemical Co., Ltd. [viscosity: 25.3 mm$^2$/S (viscosity of 2% aqueous solution was measured at 20° C. according to the Japanese Pharmacopoeia)]. The mannitol used herein is Mannitol 60 which is a D-mannitol supplied by Roquette Corporate (mean particle size: 60 μm).

The pullulan used herein is Pullulan PI-20 supplied by Hayashibara Shoji, Inc. and the polyvinyl alcohol (PVA) used herein is Shin-Etsu Poval supplied by Shin-Etsu Chemical Co., Ltd. The hydroxypropyl cellulose (HPC) used herein is HPC-L supplied by Nippon Soda Co., Ltd.; the hydroxypropyl methylcellulose (HPMC) used herein is TC-5RW supplied by Shin-Etsu Chemical Co., Ltd.; and the polyvinylpyrrolidone (PVP) used herein is Povidone K-30 supplied by ISP Corporation. The xylitol used herein is Xilite supplied by Towa Chemical Industry Co., Ltd.; and the trehalose used herein is Trehalose-P supplied by Asahi Kasei Corporation. The erythritol used herein is micronized erythritol supplied by Nikken Chemical Laboratory Co., Ltd.; and the maltitol used herein is Amalty supplied by Towa Chemical Industry Co., Ltd. The lactose used herein is 200M Lactose supplied by DMV Corporation; the lactitol used herein is Milhen supplied by Towa Chemical Industry Co., Ltd.; and the sucrose used herein is High Grade Powder Sugar supplied by Nissin Sugar Manufacturing Co., Ltd.

The cornstarch used herein is cornstarch (XX16) W supplied by Nihon Shokuhin Kako Co., LTD.; the rice starch used herein is Micropearl supplied by Shimada Chemical Co., Ltd.; the microcrystalline cellulose PH-101 used herein is Ceolus PH-101 supplied by Asahi Kasei; the microcrystalline cellulose KG-802 used herein is Ceolus KG-802 supplied by Asahi Kasei Corporation; and the anhydrous dibasic calcium phosphate used herein is Fujicalin supplied by Fuji Chemical Industry Co., Ltd. The low-substituted hydroxypropyl cellulose used herein is LH-21 supplied by Shin-Etsu Chemical Co., Ltd.; the carboxymethylcellulose used herein is Carboxymethylcellulose NS-300 supplied by Gotoku Chemical Co., Ltd.; the calcium silicate used herein is Fluorite RE supplied by Eisai Food & Chemical Co., Ltd.; the magnesium aluminometasilicate used herein is Neusilin URF2 supplied by Fuji Chemical Industry Co., Ltd.; and the crospovidone used herein is Kollidon CL supplied by BASF Takeda Vitamin. The magnesium stearate used herein is vegetable magnesium stearate supplied by Taihei Chemical Industrial Co., Ltd.

Reference Example 1

Process of Medicament-Containing Particle 1

Medicament-containing particle 1 was prepared by following the formula shown in Table 1, wherein polyvinylpyrrolidone is contained as a water-soluble Polymer. In particular, a mixture of the ingredients in Medicament-containing particle 1 was granulated while spraying 130 g of purified water with a high share mixer (manufactured by Powrex Corporation, FM-VG-05), and then the mixture was dried in a tray-type dryer. The resultant Particle was sifted through a sieve of 32 meshes (opening: 500 μm) to obtain Medicament-containing particle 1 having a mean particle size of about 150 μm.

TABLE 1

Medicament-containing particle 1

| Ingredient | Weight (g) | Content (wt %) |
|---|---|---|
| Mosapride citrate dihydrate | 264.5 | 21.2 |
| (for Mosapride citrate) | (250) | (20.0) |
| D-Mannitol | 735.5 | 58.8 |
| Polyvinylpyrrolidone | 250 | 20.0 |
| Total | 1250 | 100 |

Reference Example 2

Process of Spray-Dried Particle 1

Spray-dried particle 1 was prepared by following the formula shown in Table 2. In particular, a mixture of the ingredients in Spray-dried particle 1 was homogeneously dispersed in 186 g of water, and the mixture was spray-dried at an outlet temperature of 80° C. with a spray dryer (manufactured by Ohkawara Kakohki Co., Ltd., L-8) to obtain Spray-dried particle 1 having a white sphere-form with good fluidity.

TABLE 2

Spray-dried particle 1

| Ingredient | Weight (g) | Content (wt %) |
|---|---|---|
| D-Mannitol | 80 | 80.0 |
| Xylitol | 2 | 2.0 |
| Low-substituted hydroxypropyl cellulose | 9 | 9.0 |
| Carboxymethylcellulose | 5 | 5.0 |
| Calcium silicate | 4 | 4.0 |
| Total | 100 | 100 |

Example 1

Process of the Orally Rapidly-Disintegrating Tablet

Medicament-containing particle 1 obtained in Reference Example 1, Spray-dried particle 1 obtained in Reference Example 2 and magnesium stearate were mixed, wherein each weight/content was decided by following the formula shown in Table 3, and then the mixture was compressed at a tableting pressure of 2.0 MPa to obtain a tablet (weight per tablet: 240 mg, diameter: 8.5 mm).

TABLE 3

| Ingredient | Weight (g) | Content (wt %) |
|---|---|---|
| Medicament-containing particle 1 (Reference Example 1) | 2.5 | 10.4 |
| Spray-dried particle 1 (Reference Example 2) | 21.404 | 89.2 |
| Magnesium stearate | 0.096 | 0.4 |
| Total | 24 | 100 |

Examples 2 to 6

Following the formulas of the below Tables 4 and 5, the ingredients were mixed in the same manner as Example 1 to prepare an orally rapidly-disintegrating tablet (weight per tablet: 240 mg).

TABLE 4

Formula (weight)

(Unit: g)

| | Example | | | | |
|---|---|---|---|---|---|
| Ingredient | 2 | 3 | 4 | 5 | 6 |
| Medicament-containing particle 1 (Reference Example 1) | 2.5 | 2.5 | 2.5 | 2.5 | 2.5 |
| Spray-dried particle 1 (Reference Example 2) | 19.004 | 19.004 | 19.004 | 19.004 | 19.004 |
| Corn starch | 2.4 | — | — | — | — |
| Rice starch | — | 2.4 | — | — | 1.2 |
| Microcrystalline cellulose PH-101 | — | — | 2.4 | — | 1.2 |
| Anhydrous dibasic calcium phosphate | — | — | — | 2.4 | — |
| Magnesium stearate | 0.096 | 0.096 | 0.096 | 0.096 | 0.096 | a medicament-containing particle having a mean particle size of 150 μm to 250 μm; and then the medicament-containing particle, Spray-dried particle 1 obtained in Reference Example 2 and the other ingredients were mixed and compressed in the same manner as Example 1 to prepare each orally rapidly-disintegrating tablet (weight per tablet: 240 mg). The upper part of Tables 6 to 15 shows the formula of the medicament-containing particle and the bottom part thereof shows the formula of the orally rapidly-disintegrating tablet. Tables titled as Formula (weight) show the weight of each ingredient, and the subtotal shows the whole weight of the medicament-containing particle. Regarding tables titled as Formula (content), the upper part shows the content of each ingredient per 100 wt % of the whole medicament-containing particle (i.e. subtotal is 100 wt %), and the bottom part shows the content of each ingredient per 100 wt % of the whole orally rapidly-disintegrating tablet.

TABLE 6

Formula (weight) (Unit: g)

| | Ingredient | Example 7 | 8 | 9 | 10 | 11 |
|---|---|---|---|---|---|---|
| Medicament-containing particle | Mosapride citrate dihydrate | 264.5 | 264.5 | 264.5 | 264.5 | 264.5 |
| | (for Mosapride citrate) | (250) | (250) | (250) | (250) | (250) |
| | D-Mannitol | 750 | 750 | 750 | 750 | 750 |
| | Methylcellulose | 250 | — | — | — | — |
| | Pullulan | — | 250 | — | — | — |
| | Polyvinyl alcohol | — | — | 250 | — | — |
| | Hydroxypropyl-methylcellulose | — | — | — | 250 | — |
| | Hydroxypropyl-cellulose | — | — | — | — | 250 |
| | Subtotal | 1264.5 | 1264.5 | 1264.5 | 1264.5 | 1264.5 |
| Orally rapidly-disintegrating tablet | Above medicament-containing particle | 2.529 | 2.529 | 2.529 | 2.529 | 2.529 |
| | Spray-dried particle 1 (Reference Example 2) | 18.975 | 18.975 | 18.975 | 18.975 | 18.975 |
| | Ceolus KG-802 | 2.4 | 2.4 | 2.4 | 2.4 | 2.4 |
| | Magnesium stearate | 0.096 | 0.096 | 0.096 | 0.096 | 0.096 |
| | Total | 24 | 24 | 24 | 24 | 24 |

TABLE 7

Formula (content) (Unit: wt %)

| | Ingredient | Example 7 | 8 | 9 | 10 | 11 |
|---|---|---|---|---|---|---|
| Medicament-containing particle | Mosapride citrate dihydrate | 20.9 | 20.9 | 20.9 | 20.9 | 20.9 |
| | (for Mosapride citrate) | (19.8) | (19.8) | (19.8) | (19.8) | (19.8) |
| | D-Mannitol | 59.3 | 59.3 | 59.3 | 59.3 | 59.3 |
| | Methylcellulose | 19.8 | — | — | — | — |
| | Pullulan | — | 19.8 | — | — | — |
| | Polyvinyl alcohol | — | — | 19.8 | — | — |
| | Hydroxypropyl-methylcellulose | — | — | — | 19.8 | — |
| | Hydroxypropyl-cellulose | — | — | — | — | 19.8 |
| | Subtotal | 100 | 100 | 100 | 100 | 100 |
| Orally rapidly-disintegrating tablet | Above medicament-containing particle | 10.5 | 10.5 | 10.5 | 10.5 | 10.5 |
| | Spray-dried particle 1 (Reference Example 2) | 79.1 | 79.1 | 79.1 | 79.1 | 79.1 |

TABLE 7-continued

Formula (content)

(Unit: wt %)

| Ingredient | Example 7 | Example 8 | Example 9 | Example 10 | Example 11 |
|---|---|---|---|---|---|
| Ceolus KG-802 | 10.0 | 10.0 | 10.0 | 10.0 | 10.0 |
| Magnesium stearate | 0.4 | 0.4 | 0.4 | 0.4 | 0.4 |
| Total | 100 | 100 | 100 | 100 | 100 |

TABLE 8

Formula (weight)

(Unit: g)

| | Ingredient | Example 12 | Example 13 | Example 14 | Example 15 |
|---|---|---|---|---|---|
| Medicament-containing particle | Mosapride citrate dihydrate (for Mosapride citrate) | 264.5 (250) | 264.5 (250) | 264.5 (250) | 264.5 (250) |
| | Methylcellulose | 250 | 250 | 250 | 250 |
| | Xylitol | 750 | — | — | — |
| | Trehalose | — | 750 | — | — |
| | Lactose | — | — | 750 | — |
| | Sucrose | — | — | — | 750 |
| | Subtotal | 1264.5 | 1264.5 | 1264.5 | 1264.5 |
| Orally rapidly-disintegrating tablet | Above medicament-containing particle | 2.529 | 2.529 | 2.529 | 2.529 |
| | Spray-dried particle 1 (Reference Example 2) | 18.975 | 18.975 | 18.975 | 18.975 |
| | Ceolus KG-802 | 2.4 | 2.4 | 2.4 | 2.4 |
| | Magnesium stearate | 0.096 | 0.096 | 0.096 | 0.096 |
| | Total | 24 | 24 | 24 | 24 |

TABLE 9

Formula (content)

(Unit: wt %)

| | Ingredient | Example 12 | Example 13 | Example 14 | Example 15 |
|---|---|---|---|---|---|
| Medicament-containing particle | Mosapride citrate dihydrate (for Mosapride citrate) | 20.9 (19.8) | 20.9 (19.8) | 20.9 (19.8) | 20.9 (19.8) |
| | Methylcellulose | 19.8 | 19.8 | 19.8 | 19.8 |
| | Xylitol | 59.3 | — | — | — |
| | Trehalose | — | 59.3 | — | — |
| | Lactose | — | — | 59.3 | — |
| | Sucrose | — | — | — | 59.3 |
| | Subtotal | 100 | 100 | 100 | 100 |
| Orally rapidly-disintegrating tablet | Above medicament-containing particle | 10.5 | 10.5 | 10.5 | 10.5 |
| | Spray-dried particle 1 (Reference Example 2) | 79.1 | 79.1 | 79.1 | 79.1 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

TABLE 10

Formula (weight)

(Unit: g)

| | Ingredient | Example 16 | Example 17 | Example 18 |
|---|---|---|---|---|
| Medicament-containing particle | Mosapride citrate dihydrate (for Mosapride citrate) | 264.5 (250) | 264.5 (250) | 264.5 (250) |
| | Methylcellulose | 250 | 250 | 250 |
| | Erythritol | 750 | — | — |
| | Maltitol | — | 750 | — |
| | Lactitol | — | — | 750 |
| | Subtotal | 1264.5 | 1264.5 | 1264.5 |
| Orally rapidly-disintegrating tablet | Above medicament-containing particle | 2.529 | 2.529 | 2.529 |
| | Spray-dried particle 1 (Reference Example 2) | 18.975 | 18.975 | 18.975 |
| | Ceolus KG-802 | 2.4 | 2.4 | 2.4 |
| | Magnesium stearate | 0.096 | 0.096 | 0.096 |
| | Total | 24 | 24 | 24 |

TABLE 11

Formula (content)

(Unit: wt %)

| | Ingredient | Example 16 | Example 17 | Example 18 |
|---|---|---|---|---|
| Medicament-containing particle | Mosapride citrate dihydrate (for Mosapride citrate) | 20.9 (19.8) | 20.9 (19.8) | 20.9 (19.8) |
| | Methylcellulose | 19.8 | 19.8 | 19.8 |
| | Erythritol | 59.3 | — | — |
| | Maltitol | — | 59.3 | — |
| | Lactitol | — | — | 59.3 |
| | Subtotal | 100 | 100 | 100 |
| Orally rapidly-disintegrating tablet | Above medicament-containing particle | 10.5 | 10.5 | 10.5 |
| | Spray-dried particle 1 (Reference Example 2) | 79.1 | 79.1 | 79.1 |
| | Ceolus KG-802 | 10.0 | 10.0 | 10.0 |
| | Magnesium stearate | 0.4 | 0.4 | 0.4 |
| | Total | 100 | 100 | 100 |

TABLE 12

Formula (weight)

(Unit: g)

| | Ingredient | Example 19 | Example 20 | Example 21 | Example 22 |
|---|---|---|---|---|---|
| Medicament-containing particle | Mosapride citrate dihydrate (for Mosapride citrate) | 105.8 (100) | 105.8 (100) | 105.8 (100) | 52.9 (50) |
| | D-Mannitol | 300 | 700 | 1000 | 1000 |
| | Methylcellulose | 800 | 100 | 100 | 50 |
| | Subtotal | 1205.8 | 905.8 | 1205.8 | 1102.9 |
| Orally rapidly-disintegrating tablet | Above medicament-containing particle | 6.029 | 4.529 | 6.029 | 11.029 |
| | Spray-dried particle 1 (Reference Example 2) | 15.475 | 16.975 | 15.475 | 15.851 |
| | Ceolus KG-802 | 2.4 | 2.4 | 2.4 | 3 |
| | Magnesium stearate | 0.096 | 0.096 | 0.096 | 0.12 |
| | Total | 24 | 24 | 24 | 30 |

TABLE 13

Formula (content)

(Unit: wt %)

| | Ingredient | Example 19 | Example 20 | Example 21 | Example 22 |
|---|---|---|---|---|---|
| Medicament-containing particle | Mosapride citrate dihydrate (for Mosapride citrate) | 8.8 (8.3) | 11.7 (11.0) | 8.8 (8.3) | 4.8 (4.5) |
| | D-Mannitol | 24.9 | 77.3 | 82.9 | 90.7 |
| | Methyl-cellulose | 66.3 | 11.0 | 8.3 | 4.5 |
| | Subtotal | 100 | 100 | 100 | 100 |
| Orally rapidly-disintegrating tablet | Above medicament-containing particle | 25.1 | 18.9 | 25.1 | 36.8 |
| | Spray-dried particle 1 (Reference Example 2) | 64.5 | 70.7 | 64.5 | 52.8 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

TABLE 15

Formula (content)

(Unit: wt %)

| | Ingredient | Example 23 | Example 24 | Example 25 | Example 26 |
|---|---|---|---|---|---|
| Medicament-containing particle | Mosapride citrate dihydrate (for Mosapride citrate) | 34.6 (32.7) | 24.8 (23.5) | 17.5 (16.5) | 15.0 (14.2) |
| | D-Mannitol | 32.7 | 70.5 | 49.5 | 42.5 |
| | Methyl-cellulose | 32.7 | 4.7 | 33.0 | 42.5 |
| | Subtotal | 100 | 100 | 100 | 100 |
| Orally rapidly-disintegrating tablet | Above medicament-containing particle | 6.4 | 8.9 | 12.6 | 14.7 |
| | Spray-dried particle 1 (Reference Example 2) | 83.2 | 80.7 | 77.0 | 74.9 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

TABLE 14

Formula (weight)

(Unit: g)

| | Ingredient | Example 23 | Example 24 | Example 25 | Example 26 |
|---|---|---|---|---|---|
| Medicament-containing particle | Mosapride citrate dihydrate (for Mosapride citrate) | 26.45 (25) | 15.87 (15) | 10.58 (10) | 10.58 (10) |
| | D-Mannitol | 25 | 45 | 30 | 30 |
| | Methyl-cellulose | 25 | 3 | 20 | 30 |
| | Subtotal | 76.45 | 63.87 | 60.58 | 70.58 |
| Orally rapidly-disintegrating tablet | Above medicament-containing particle | 1.529 | 2.129 | 3.029 | 3.529 |
| | Spray-dried particle 1 (Reference Example 2) | 19.975 | 19.375 | 18.475 | 17.975 |
| | Ceolus KG-802 | 2.4 | 2.4 | 2.4 | 2.4 |
| | Magnesium stearate | 0.096 | 0.096 | 0.096 | 0.096 |
| | Total | 24 | 24 | 24 | 24 |

Reference Example 3

Process of Medicament-Containing Particle 2

Medicament-containing particle 2 was prepared by following the formula shown in Table 16, wherein methylcellulose is contained as a water-soluble polymer. In particular, the ingredients in Medicament-containing particle 2 were mixed in the same manner as Reference Example 1 to obtain a particle, and then the particle was sifted through a sieve of 32 meshes (opening: 500 μm) to obtain Medicament-containing particle 2 having a mean particle size of about 150 μm to 250 μm.

TABLE 16

| Medicament-containing particle 2 | | |
|---|---|---|
| Ingredient | Weight (g) | Content (wt %) |
| Mosapride citrate dihydrate | 264.5 | 20.9 |
| (for Mosapride citrate) | (250) | (19.8) |
| D-Mannitol | 750 | 59.3 |
| Methylcellulose | 250 | 19.8 |
| Total | 1264.5 | 100 |

Example 27 and Comparative Example 1

Following the formulas of the below Tables 1.7 and 18, the ingredients in spray-dried particle were mixed in the same manner as Reference Example 2 to obtain a spray-dried particle, and then the spray-dried particle were mixed with other ingredients in the same manner as Example 1 to prepare each orally rapidly-disintegrating tablet (weight per tablet: 240 mg). Table 17 shows, the weight of each ingredient, and the subtotal shows the whole weight of the spray-dried particle. Regarding the spray-dried particle, Table 18 shows the content of each ingredient per 100 wt % of the whole spray-dried particle (i.e. subtotal is 100 wt %). Regarding the orally rapidly-disintegrating tablet, Table 18 shows the content of each ingredient per 100 wt % of the whole orally rapidly-disintegrating tablet.

TABLE 17

Formula (weight)

| | Ingredient | Example 27 | (Unit: g) Comparative Example 1 |
|---|---|---|---|
| Spray-dried particle | D-Mannitol | 78 | 60 |
| | Xylitol | 2 | 5 |
| | Low-substituted hydroxypropyl cellulose | 9 | — |
| | Carboxymethylcellulose | 5 | — |
| | Magnesium aluminometasilicate | 6 | — |
| | Anhydrous dibasic calcium phosphate | — | 4 |
| | Crospovidone | — | 13 |
| | Microcrystalline cellulose PH-101 | — | 18 |
| | Subtotal | 100 | 100 |
| Orally rapidly-disintegrating tablet | Medicament-containing particle 2 (Reference Example 3) | 2.529 | 2.529 |
| | Above spray-dried particle | 18.975 | 18.975 |
| | Ceolus KG-802 | 2.4 | 2.4 |
| | Magnesium stearate | 0.096 | 0.096 |
| | Total | 24 | 24 |

TABLE 18

Formula (content)

| | Ingredient | Example 27 | (Unit: wt %) Comparative Example 1 |
|---|---|---|---|
| Spray-dried particle | D-Mannitol | 78.0 | 60.0 |
| | Xylitol | 2.0 | 5.0 |
| | Low-substituted hydroxypropyl cellulose | 9.0 | — |
| | Carboxymethylcellulose | 5.0 | — |
| | Magnesium aluminometasilicate | 6.0 | — |
| | Anhydrous dibasic calcium phosphate | — | 4.0 |
| | Crospovidone | — | 13.0 |
| | Microcrystalline cellulose PH-101 | — | 18.0 |
| | Subtotal | 100 | 100 |
| Orally rapidly-disintegrating tablet | Medicament-containing particle 2 (Reference Example 3) | 10.5 | 10.5 |
| | Above spray-dried particle | 79.1 | 79.1 |
| | Ceolus KG-802 | 10.0 | 10.0 |
| | Magnesium stearate | 0.4 | 0.4 |
| | Total | 100 | 100 |

Examples 28 to 43

Following the formulas of the below Tables 19 to 26, the ingredients in spray-dried particle were mixed in the same manner as Reference Example 2 to prepare a spray-dried particle, and then the spray-dried particle was mixed with other ingredients in the same manner as Example 1 to prepare each orally rapidly-disintegrating tablet (weight per tablet: 240 mg).

TABLE 19

Formula (weight)

| | | | | Example | | (Unit: g) |
|---|---|---|---|---|---|---|
| | Ingredient | | 28 | 29 | 30 | 31 |
| Spray-dried particle | D-Mannitol | | 81 | 82 | 81 | 86 |
| | Xylitol | | 2 | 0 | 1 | 2 |
| | Low-substituted hydroxypropyl cellulose | | 9 | 9 | 9 | 3 |
| | Carboxymethylcellulose | | 5 | 5 | 5 | 5 |
| | Calcium silicate | | 3 | 4 | 4 | 4 |
| | Subtotal | | 100 | 100 | 100 | 100 |
| Orally rapidly-disintegrating tablet | Medicament-containing particle 2 (Reference Example 3) | | 2.529 | 2.529 | 2.529 | 2.529 |
| | Above spray-dried particle | | 18.975 | 18.975 | 18.975 | 18.975 |
| | Ceolus KG-802 | | 2.4 | 2.4 | 2.4 | 2.4 |
| | Magnesium stearate | | 0.096 | 0.096 | 0.096 | 0.096 |
| | Total | | 24 | 24 | 24 | 24 |

TABLE 20

Formula (content)

(Unit: wt %)

| | Ingredient | Example 28 | Example 29 | Example 30 | Example 31 |
|---|---|---|---|---|---|
| Spray-dried particle | D-Mannitol | 81.0 | 82.0 | 81.0 | 86.0 |
| | Xylitol | 2.0 | 0.0 | 1.0 | 2.0 |
| | Low-substituted hydroxypropyl cellulose | 9.0 | 9.0 | 9.0 | 3.0 |
| | Carboxymethyl-cellulose | 5.0 | 5.0 | 5.0 | 5.0 |
| | Calcium silicate | 3.0 | 4.0 | 4.0 | 4.0 |
| | Subtotal | 100 | 100 | 100 | 100 |
| Orally rapidly-disintegrating tablet | Medicament-containing particle 2 (Reference Example 3) | 10.5 | 10.5 | 10.5 | 10.5 |
| | Above spray-dried particle | 79.1 | 79.1 | 79.1 | 79.1 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

TABLE 21

Formula (weight)

(Unit: g)

| | Ingredient | Example 32 | Example 33 | Example 34 | Example 35 |
|---|---|---|---|---|---|
| Spray-dried particle | D-Mannitol | 86 | 69 | 69 | 76 |
| | Xylitol | 2 | 2 | 2 | 2 |
| | Low-substituted hydroxypropyl cellulose | 5 | 15 | 10 | 9 |
| | Carboxymethyl-cellulose | 3 | 10 | 15 | 5 |
| | Calcium silicate | 4 | 4 | 4 | 8 |
| | Subtotal | 100 | 100 | 100 | 100 |
| Orally rapidly-disintegrating tablet | Medicament-containing particle 2 (Reference Example 3) | 2.529 | 2.529 | 2.529 | 2.529 |
| | Above spray-dried particle | 18.975 | 18.975 | 18.975 | 18.975 |
| | Ceolus KG-802 | 2.4 | 2.4 | 2.4 | 2.4 |
| | Magnesium stearate | 0.096 | 0.096 | 0.096 | 0.096 |
| | Total | 24 | 24 | 24 | 24 |

TABLE 22

Formula (content)

(Unit: wt %)

| | Ingredient | Example 32 | Example 33 | Example 34 | Example 35 |
|---|---|---|---|---|---|
| Spray-dried particle | D-Mannitol | 86.0 | 69.0 | 69.0 | 76.0 |
| | Xylitol | 2.0 | 2.0 | 2.0 | 2.0 |
| | Low-substituted hydroxypropyl cellulose | 5.0 | 15.0 | 10.0 | 9.0 |
| | Carboxymethyl-cellulose | 3.0 | 10.0 | 15.0 | 5.0 |
| | Calcium silicate | 4.0 | 4.0 | 4.0 | 8.0 |
| | Subtotal | 100 | 100 | 100 | 100 |
| Orally rapidly-disintegrating tablet | Medicament-containing particle 2 (Reference Example 3) | 10.5 | 10.5 | 10.5 | 10.5 |
| | Above spray-dried particle | 79.1 | 79.1 | 79.1 | 79.1 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

TABLE 23

Formula (weight)

(Unit: g)

| | Ingredient | Example 36 | Example 37 | Example 38 | Example 39 |
|---|---|---|---|---|---|
| Spray-dried particle | D-Mannitol | 84 | 72 | 77 | 76 |
| | Xylitol | 2 | 2 | 5 | 0 |
| | Low-substituted hydroxypropyl cellulose | 9 | 9 | 9 | 10 |
| | Carboxymethyl-cellulose | 5 | 5 | 5 | 10 |
| | Calcium silicate | 0 | 12 | 4 | 4 |
| | Subtotal | 100 | 100 | 100 | 100 |
| Orally rapidly-disintegrating tablet | Medicament-containing particle 2 (Reference Example 3) | 2.529 | 2.529 | 2.529 | 2.529 |
| | Above spray-dried particle | 18.975 | 18.975 | 18.975 | 18.975 |
| | Ceolus KG-802 | 2.4 | 2.4 | 2.4 | 2.4 |
| | Magnesium stearate | 0.096 | 0.096 | 0.096 | 0.096 |
| | Total | 24 | 24 | 24 | 24 |

TABLE 24

Formula (content)

(Unit: wt %)

| | Ingredient | Example 36 | Example 37 | Example 38 | Example 39 |
|---|---|---|---|---|---|
| Spray-dried particle | D-Mannitol | 84.0 | 72.0 | 77.0 | 76.0 |
| | Xylitol | 2.0 | 2.0 | 5.0 | 0.0 |
| | Low-substituted hydroxypropyl cellulose | 9.0 | 9.0 | 9.0 | 10.0 |
| | Carboxymethyl-cellulose | 5.0 | 5.0 | 5.0 | 10.0 |
| | Calcium silicate | 0.0 | 12.0 | 4.0 | 4.0 |
| | Subtotal | 100 | 100 | 100 | 100 |

TABLE 24-continued

Formula (content)

| | | (Unit: wt %) Example | | | |
|---|---|---|---|---|---|
| | Ingredient | 36 | 37 | 38 | 39 |
| Orally rapidly-disintegrating tablet | Medicament-containing particle 2 (Reference Example 3) | 10.5 | 10.5 | 10.5 | 10.5 |
| | Above spray-dried particle | 79.1 | 79.1 | 79.1 | 79.1 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

TABLE 25

Formula (weight)

| | | (Unit: g) Example | | | |
|---|---|---|---|---|---|
| | Ingredient | 40 | 41 | 42 | 43 |
| Spray-dried particle | D-Mannitol | 86 | 80 | 80 | 79 |
| | Xylitol | 0 | 1 | 1 | 2 |
| | Low-substituted hydroxypropyl cellulose | 5 | 5 | 10 | 5 |
| | Carboxymethyl-cellulose | 5 | 10 | 5 | 10 |
| | Calcium silicate | 4 | 4 | 4 | 4 |
| | Subtotal | 100 | 100 | 100 | 100 |
| Orally rapidly-disintegrating tablet | Medicament-containing particle 2 (Reference Example 3) | 2.529 | 2.529 | 2.529 | 2.529 |
| | Above spray-dried particle | 18.975 | 18.975 | 18.975 | 18.975 |
| | Ceolus KG-802 | 2.4 | 2.4 | 2.4 | 2.4 |
| | Magnesium stearate | 0.096 | 0.096 | 0.096 | 0.096 |
| | Total | 24 | 24 | 24 | 24 |

TABLE 26

Formula (content)

| | | (Unit: wt %) Example | | | |
|---|---|---|---|---|---|
| | Ingredient | 40 | 41 | 42 | 43 |
| Spray-dried particle | D-Mannitol | 86.0 | 80.0 | 80.0 | 79.0 |
| | Xylitol | 0.0 | 1.0 | 1.0 | 2.0 |
| | Low-substituted hydroxypropyl cellulose | 5.0 | 5.0 | 10.0 | 5.0 |
| | Carboxymethyl-cellulose | 5.0 | 10.0 | 5.0 | 10.0 |
| | Calcium silicate | 4.0 | 4.0 | 4.0 | 4.0 |
| | Subtotal | 100 | 100 | 100 | 100 |
| Orally rapidly-disintegrating tablet | Medicament-containing particle 2 (Reference Example 3) | 10.5 | 10.5 | 10.5 | 10.5 |
| | Above spray-dried particle | 79.1 | 79.1 | 79.1 | 79.1 |
| | Ceolus KG-802 | 10.0 | 10.0 | 10.0 | 10.0 |
| | Magnesium stearate | 0.4 | 0.4 | 0.4 | 0.4 |
| | Total | 100 | 100 | 100 | 100 |

Test Example 1

The properties of the tablets prepared in Examples and Comparative Example were evaluated to obtain the results shown in Tables 27 and 28.

In particular, the disintegration time was measured under the standard condition of an orally disintegrating tablet tester (manufactured by Toyama Sangyo Co., Ltd.) which is commercially available. In addition, the hardness of the tablets was measured immediately after the tablet was prepared and also after the tablet was humidified.

The results are shown in the following table. The orally rapidly-disintegrating tablet obtained in each of Examples had a suitable hardness (i.e. 30 N or more) and a sufficient disintegration property in the oral cavity (i.e. the disintegration time was 40 seconds or less). Furthermore, in the case of Comparative Example (i.e. a tablet which does not comprise carboxymethylcellulose in the spray-dried particle), the hardness maintenance rate was 49%; whereas in the cases of Examples (i.e. the orally rapidly-disintegrating tablets of the present invention), the hardness maintenance rate was at least 60% or more, and in fact, 70% or more and 80% or more in many cases. Thus, the hardness maintenance rate was significantly higher in the tablets of Examples than in the tablet of Comparative Example.

TABLE 27 AND TABLE 28

| | Tableting pressure (Mpa) *1 | Disintegration time (s) *2 | Hardness (N) *3 | Hardness after humidification (N) *4 | Hardness maintenance rate (%) *5 |
|---|---|---|---|---|---|
| Ex. 1 | 2.0 | 30 | 38 | 44 | 116 |
| Ex. 2 | 3.0 | 29 | 59 | 53 | 90 |
| Ex. 3 | 3.0 | 39 | 72 | 68 | 94 |
| Ex. 4 | 2.0 | 31 | 57 | 47 | 82 |
| Ex. 5 | 2.0 | 23 | 38 | 29 | 76 |
| Ex. 6 | 2.5 | 37 | 68 | 49 | 72 |
| Ex. 7 | 2.0 | 24 | 52 | 40 | 77 |
| Ex. 8 | 2.0 | 28 | 42 | 40 | 95 |
| Ex. 9 | 2.0 | 18 | 40 | 40 | 100 |
| Ex. 10 | 2.0 | 22 | 43 | 36 | 84 |
| Ex. 11 | 2.0 | 24 | 40 | 39 | 98 |
| Ex. 12 | 2.0 | 34 | 42 | 38 | 90 |
| Ex. 13 | 2.0 | 56 | 45 | 38 | 84 |
| Ex. 14 | 2.0 | 33 | 41 | 38 | 93 |
| Ex. 15 | 2.0 | 46 | 42 | 40 | 95 |
| Ex. 16 | 2.0 | 32 | 35 | 27 | 77 |
| Ex. 17 | 2.0 | 40 | 42 | 34 | 81 |
| Ex. 18 | 2.0 | 35 | 43 | 35 | 81 |

TABLE 27 AND TABLE 28-continued

|  | Tableting pressure (Mpa) *1 | Disintegration time (s) *2 | Hardness (N) *3 | Hardness after humidification (N) *4 | Hardness maintenance rate (%) *5 |
|---|---|---|---|---|---|
| Ex. 19 | 2.3 | 63 | 49 | 38 | 78 |
| Ex. 20 | 3.0 | 31 | 46 | 46 | 100 |
| Ex. 21 | 3.5 | 37 | 57 | 39 | 68 |
| Ex. 22 | 3.5 | 38 | 61 | 38 | 62 |
| Ex. 23 | 3.0 | 51 | 46 | 58 | 126 |
| Ex. 24 | 2.5 | 26 | 45 | 46 | 102 |
| Ex. 25 | 2.5 | 24 | 46 | 41 | 89 |
| Ex. 26 | 2.5 | 35 | 44 | 41 | 93 |
| Ex. 27 | 2.5 | 36 | 45 | 42 | 93 |
| Ex. 28 | 4.5 | 29 | 48 | 39 | 81 |
| Ex. 29 | 3.0 | 22 | 44 | 37 | 84 |
| Ex. 30 | 2.5 | 22 | 48 | 40 | 83 |
| Ex. 31 | 3.0 | 35 | 48 | 42 | 88 |
| Ex. 32 | 3.0 | 34 | 43 | 40 | 93 |
| Ex. 33 | 2.5 | 24 | 51 | 43 | 84 |
| Ex. 34 | 2.8 | 24 | 46 | 34 | 74 |
| Ex. 35 | 2.2 | 26 | 47 | 38 | 81 |
| Ex. 36 | 4.2 | 24 | 48 | 37 | 77 |
| Ex. 37 | 1.5 | 26 | 47 | 44 | 94 |
| Ex. 38 | 2.0 | 32 | 42 | 33 | 79 |
| Ex. 39 | 3.2 | 23 | 41 | 33 | 80 |
| Ex. 40 | 2.8 | 20 | 45 | 34 | 76 |
| Ex. 41 | 2.8 | 26 | 44 | 42 | 95 |
| Ex. 42 | 2.5 | 25 | 49 | 40 | 82 |
| Ex. 43 | 2.5 | 22 | 44 | 30 | 68 |
| Comparative Ex. 1 | 2.0 | 29 | 43 | 21 | 49 |

*1: The pressure on the punch when compressing into a tablet was recorded using a pressure gage attached to the tablet press machine (manufactured by RIKEN, Oil Hydraulic Press).
*2: The time that the weight (diameter: 15 mm, weight: 15 g) reaches to the mesh sheet (i.e. the tablet is disintegrated by the weight) was measured on an orally disintegrating tablet tester (manufactured by Toyama Sangyo Co., Ltd., ODT-101).
*3: The hardness was measured on a tablet hardness tester (manufactured by Toyama Sangyo Co., Ltd., TH-203MP).
*4: The hardness of the tablets after storing for one day (25° C./75% RH) was measured on a tablet hardness tester (manufactured by Toyama Sangyo Co., Ltd., TH-203MP).
*5: The hardness maintenance rate was calculated as follows: Hardness after humidification/Hardness × 100 (%)

INDUSTRIAL APPLICABILITY

Regarding medicaments with unpleasant taste, the present invention can provide a tablet comprising such medicament which has the following properties:

a suitable hardness so that the tablet can be handled without any difficulty in the period from the formulation of the tablet to the administration thereof (in particular, a tablet which can maintain the hardness thereof when it is subjected to a humidified condition), a small size, without any unpleasant taste, a pleasant feeling in a mouth after administration, and an excellent disintegration character in the oral cavity and an excellent dissolution character in the gastrointestinal tract; and a bulk-production process thereof.

The invention claimed is:

1. An orally rapidly-disintegrating tablet comprising the following particles (1) and (2):
   (1) a medicament-containing particle comprising the following ingredients (a) to (c):
      (a) a medicament
      (b) a water-soluble polymer, and
      (c) a sugar or sugar alcohol,
   wherein all of the ingredients (a) to (c) are granulated and then particulated, and
   (2) a spray-dried particle comprising the following ingredients (d) to (f):
      (d) mannitol, or mannitol and xylitol
      (e) carboxymethylcellulose, and
      (f) a disintegrant,
   wherein all of the ingredients (d) to (f) are dispersed in a solvent for dispersion and then spray-dried.

2. The orally rapidly-disintegrating tablet of claim 1, wherein the water-soluble polymer (b) is at least one compound selected from the group consisting of polyvinylpyrrolidone, methylcellulose, pullulan, polyvinyl alcohol, hydroxypropyl methylcellulose, and hydroxypropyl cellulose.

3. The orally rapidly-disintegrating tablet of claim 2, wherein the water-soluble polymer (b) is at least one compound selected from the group consisting of methylcellulose, pullulan, polyvinyl alcohol, and hydroxypropyl cellulose.

4. The orally rapidly-disintegrating tablet of claim 1, wherein the sugar or sugar alcohol (c) is at least one compound selected from the group consisting of mannitol, xylitol, lactose, erythritol, trehalose, sucrose, maltitol, and lactitol.

5. The orally rapidly-disintegrating tablet of claim 4, wherein the sugar or sugar alcohol (c) is at least one compound selected from the group consisting of mannitol, xylitol, lactose, erythritol, and lactitol.

6. The orally rapidly-disintegrating tablet of claim 1, wherein the disintegrant (f) is at least one compound selected from the group consisting of a low-substituted hydroxypropyl cellulose, croscarmellose sodium, microcrystalline cellulose, carmellose calcium, hydroxypropyl starch, and rice starch.

7. The orally rapidly-disintegrating tablet of claim 6, wherein the disintegrant (f) is a low-substituted hydroxypropyl cellulose.

8. The orally rapidly-disintegrating tablet of claim 1, wherein the spray-dried particle (2) further comprises ingredient (g):
   (g) an inorganic compound,
and all of the ingredients (d) to (g) are dispersed in the solvent for dispersion and then spray-dried.

9. The orally rapidly-disintegrating tablet of claim 8, wherein the inorganic compound (g) is at least one compound selected from the group consisting of magnesium aluminometasilicate, magnesium aluminosilicate, anhydrous silicic acid, light anhydrous silicic acid, calcium silicate, and dibasic calcium phosphate.

10. The orally rapidly-disintegrating tablet of claim 1, wherein each content of:
   (a) the medicament is 1 wt % to 30 wt %,
   (b) the water-soluble polymer is 3 wt % to 45 wt %, and
   (c) the sugar or sugar alcohol is 40 wt % to 90 wt %,
per 100 wt % of the whole weight of the medicament-containing particle (1).

11. The orally rapidly-disintegrating tablet of claim 1, wherein each content of:
   (d) the mannitol, or mannitol and xylitol is 65 wt % to 95 wt %,
   (e) the carboxymethylcellulose is 1 wt % to 20 wt %, and
   (f) the disintegrant is 1 wt % to 20 wt %,
per 100 wt % of the whole weight of the spray-dried particle (2).

12. The orally rapidly-disintegrating tablet of claim 11, wherein the spray-dried particle (2) further comprises:
   (g) an inorganic compound in an amount of 0.01 wt % to 15 wt %,
per 100 wt % of the whole weight of the spray-dried particle (2).

13. The orally rapidly-disintegrating tablet of claim 1, wherein the medicament (a) is 4-amino-5-chloro-2-ethoxy-N-[[4-(4-fluorobenzyl)-2-morpholinyl]-methyl]benzamide.

14. The orally rapidly-disintegrating tablet of claim 1, wherein each content of:
- the medicament-containing particle (1) is 5 wt % to 37 wt %, and
- the spray-dried particle (2) is 15 wt % to 90 wt %, per 100 wt % of the whole weight of the orally rapidly-disintegrating tablet.

* * * * *